United States Patent
Wiley

(10) Patent No.: US 12,268,634 B2
(45) Date of Patent: Apr. 8, 2025

(54) FLEXIBLE/EXPANDABLE PHACOEMULSIFICATION TIP

(71) Applicant: William F. Wiley, Chagrin Falls, OH (US)

(72) Inventor: William F. Wiley, Chagrin Falls, OH (US)

( * ) Notice: Subject to any disclaimer, the term of this patent is extended or adjusted under 35 U.S.C. 154(b) by 311 days.

(21) Appl. No.: 17/464,622

(22) Filed: Sep. 1, 2021

(65) Prior Publication Data

US 2022/0054312 A1 Feb. 24, 2022

Related U.S. Application Data

(63) Continuation of application No. 16/133,223, filed on Sep. 17, 2018, now Pat. No. 11,110,004.

(60) Provisional application No. 62/559,914, filed on Sep. 18, 2017.

(51) Int. Cl.
| | |
|---|---|
| *A61F 9/007* | (2006.01) |
| *A61L 29/12* | (2006.01) |
| *A61M 1/00* | (2006.01) |
| *A61M 25/00* | (2006.01) |

(52) U.S. Cl.
CPC ........ *A61F 9/00745* (2013.01); *A61L 29/126* (2013.01); *A61M 1/84* (2021.05); *A61F 9/007* (2013.01); *A61F 9/00709* (2013.01); *A61M 2025/0024* (2013.01); *A61M 2210/0612* (2013.01)

(58) Field of Classification Search
CPC ........ A61M 2025/0024; A61F 9/00754; A61F 9/007; A61F 9/00709
See application file for complete search history.

(56) References Cited

U.S. PATENT DOCUMENTS

| | | | |
|---|---|---|---|
| 8,597,277 B2 | 12/2013 | Lenker et al. | |
| 9,060,845 B2 | 6/2015 | Van Valen et al. | |
| 9,522,253 B2 * | 12/2016 | Gandras | A61J 15/0046 |
| 10,016,301 B2 * | 7/2018 | Silvestrini | A61M 37/00 |
| 2002/0095113 A1 | 7/2002 | Kishimoto | |
| 2015/0038894 A1 | 2/2015 | Urich | |

OTHER PUBLICATIONS

Application and File History for U.S. Appl. No. 16/133,223, filed Sep. 17, 2018. Inventor: William F. Wiley.

* cited by examiner

*Primary Examiner* — Nathan R Price
*Assistant Examiner* — Tania Ismail
(74) *Attorney, Agent, or Firm* — DeWitt LLP

(57) ABSTRACT

A phacoemulsification cutting tip, including a rigid tubular portion and a flexible and expandable tip portion located distal to the rigid tubular portion. The flexible and expandable tip portion presents an axial length and an unexpanded radius and is formed such that the axial length shortens while the unexpanded radius increases when differential pressure due to an occlusion of an opening of the flexible tip portion exists.

18 Claims, 5 Drawing Sheets

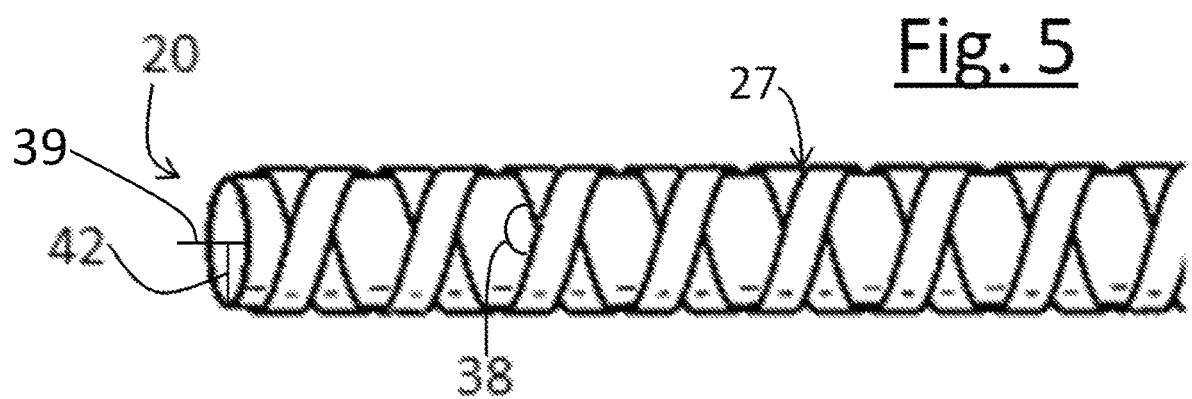

FLEXIBLE/EXPANDABLE PHACOEMULSIFICATION TIP

RELATED APPLICATION

This application is a continuation of application Ser. No. 16/133,223, filed Sep. 17, 2018, entitled "Flexible/Expandable Phacoemulsification Tip," which claims the benefit of U.S. Provisional Application No. 62/559,914, filed Sep. 18, 2017, entitled "Flexible/Expandable Phacoemulsification Tip," each of which is hereby fully incorporated herein by reference.

TECHNICAL FIELD

Embodiments of the present invention generally relate to phacoemulsification surgical instruments, and more particularly relate to phacoemulsification tips designed to aspirate tissue of the crystalline lens from the eye.

BACKGROUND

Phacoemulsification is a commonly practiced ocular surgical procedure for removing cataracts. Cataracts, a leading cause of blindness worldwide, occur when the natural crystalline lens of the eye becomes cloudy or opacified. Cataracts are generally considered to be caused by protein aggregation and accumulation in the natural crystalline lens, causing light scattering. The interference with the passage of light through the natural crystalline lens causes images to become cloudy and distorted, thereby diminishing visual acuity. Severe diminishment of visual acuity from cataracts can lead to an increase in auto accidents, falls, and other social problems. Therefore, surgical procedures, including phacoemulsification, have been developed to treat cataracts and to restore lost vision. Generally, cataract extraction surgical procedures enable a surgeon to remove the clouded natural crystalline lens and insert an artificial intraocular lens implant to replace the focusing power of the removed natural lens.

The conventional phacoemulsification procedure emulsifies or fragments the affected lens with the use of an ultrasonic hand-held device. Typically, the ultrasonic device includes a needle like tip, which is inserted into an incision made near the outer edge of the cornea of the eye. Once inserted, the tip vibrates ultrasonically to fragment the lens for removal by aspiration. After the natural lens is fragmented and substantially removed, an artificial prescription intraocular lens is implanted through the incision to replace the natural lens and its focusing power.

The hand-held device tip includes an irrigation sleeve and an aspiration channel. The aspiration channel is housed within a hollow cross sectional area of the needle tip and is operably coupled to a source of suction to aspirate fluid and fragmented tissue during the procedure. The irrigation sleeve usually surrounds the needle tip and is operably coupled to a source of a liquid such as a balanced salt solution which is delivered into the eye to aid in flushing and aspirating lens fragments and to replace fluid withdrawn or lost from the anterior chamber of the eye during the surgical procedure.

Phacoemulsification procedures have proven highly effective, however, more advanced or denser cataracts can cause complications. The hardness of the lens nucleus varies greatly, but generally, the lens nucleus becomes harder and denser as a cataract develops and progresses, thus making removal of the lens nucleus more difficult. The prior art has attempted to address these concerns and provide increased efficiency.

In one conventional approach, the aspiration channel provides suction to aspirate fluid and tissue from the anterior chamber of the eye. The aspiration of fluid draws fragmented pieces of the lens cortex and material of the lens nucleus to the aspiration channel for removal. However, larger lens fragments and harder denser pieces of the nucleus may be more difficult to aspirate through the narrow aspiration channel, which can prolong the removal process. Furthermore, the aspiration of larger lens fragments or hard dense pieces of the nucleus can sometimes temporarily occlude the aspiration channel. An occlusion of the aspiration channel causes the vacuum level within the aspiration tubing to rise until the negative pressure generated overcomes the resistance of the occlusion, which can cause a rapid flow increase into and through the aspiration channel. These issues can have negative effects, including surgery complications and damage to ocular structures.

Further, lens fragments that are too large to be or that are not yet aspirated into the aspiration channel may move about within the eye and interfere with the surgeon's ability to see the lens and other structures of the eye.

Thus, there remains room for improvement in phacoemulsification devices and to address problems that still exist in phacoemulsification techniques.

SUMMARY

Embodiments of the invention solve many of the above discussed problems and include a phacoemulsification aspiration tip having a flexible and expandable structure to encourage and facilitate the passage of lens fragments that are separated from the lens during phacoemulsification to be aspirated into the tip and out of the eye. Embodiments of the aspiration tip structure may also facilitate or encourage aspiration of fluid from the eye and fluid flow into and through the aspiration channel.

It has been observed during phacoemulsification surgery that when a phacoemulsification tip is placed in proximity of or in contact with portions of the crystalline lens inside the eye, there is a tendency for lens fragments to move away from the phacoemulsification tip due to the ultrasonic vibration of the tip. On occasion, fragments of the lens are aspirated into the aspiration tip but then move out of the aspiration tip again thereafter requiring that they be aspirated a second time or further times before they are actually removed from the eye. Larger lens fragments and hard dense pieces of the nucleus can exacerbate this issue and prolong the tissue removal process. Lens fragments and pieces of the nucleus not yet aspirated may circulate about within the aqueous humor in the anterior chamber and interfere with the surgeon's ability to see the lens and other structures of the eye.

As is known to those skilled in the art, it is preferable to decrease the time spent removing tissue from the eye and minimize interferences with the surgeon's ability to see the lens and other structures of the eye. Additional time spent in phacoemulsification can lead to additional application of ultrasonic energy to the eye and a greater potential that the cells of the corneal endothelium or other structures will be damaged by excess ultrasonic energy. Furthermore, interference with the surgeon's ability to see the lens and other structures of the eye can complicate the surgery and have other negative effects. Accordingly, any improvement made to the phacoemulsification tip to facilitate the removal of material by aspiration from the eye is expected to minimize the time necessary for tissue removal and reduce the interference with the surgeon's ability to see the lens and other structures of the eye. It is expected that embodiments of the invention will minimize the tendency for tissue fragments to move about within the eye and will facilitate the removal of lens material through the aspiration channel of the phacoemulsification tip.

According to an example embodiment of the invention, a phacoemulsification device includes at least one aspiration channel with a flexible and expandable tip. In an example embodiment, the tip includes a woven structure extending at least partially from a distal end toward a proximal end of the expandable tip. The proximal end of the tip is operably coupled to the phacoemulsification handpiece. The phacoemulsification device terminates at the distal end of the tip. The distal end of the tip can have a cylindrical shape. The distal end of the tip is flexible and expandable for at least a portion of its length.

According to another embodiment of the invention, the specific, expandable portion includes a woven structure that can take the form of a cylindrical, helically wound, biaxial braid. The woven structure can be coated with or embedded, for example, in an elastomeric polymer. The woven structure includes an exterior surface and an interior surface. The exterior surface covers the entire exterior circumference of the tip. The interior surface covers the entire interior circumference of the tip. The lumen of the tip includes the internal cavity of the tip defined by the interior surface. The distal end of the tip forms the mouth of the opening which leads into the lumen. The mouth of the opening and the lumen are in fluid communication with a suction source to deliver suction at the distal end of the tip.

According to another embodiment of the invention, the woven structure includes spiral or helix shaped material. The helix shaped material is interlaced to form the woven structure. The helix shaped material can include metal filaments, polymer fibers, polyaramid, para-aramid or other suitable material. The cylindrical woven structure is formed in such a way that the length of the cylinder can shorten along the axis of the cylinder. As the length of the cylindrical woven structure shortens, the distal end is drawn towards the proximal end. As the length of the cylindrical woven structure shortens, the distal end expands radially outward so that the radius of the distal end increases. As the length of the cylindrical woven structure shortens, an angle between the helixes at their crossing points increases. In general, the woven structure is formed in such a way that the distal radius of the tip increases as the length of the tip shortens. Furthermore, the aspiration tip is formed in such a way that aspiration of tissue fragments can cause the length of the tip to shorten, which can cause the distal radius of the distal end to lengthen. The woven structure has a resilient nature so that the aspiration tip tends to return to its original length and cylindrical shape following an axial shortening.

The aspiration of larger tissue fragments can cause an occlusion at the distal end of the tip. An occlusion can cause a relative increase in negative pressure inside the lumen generated by a vacuum source. An increase in negative pressure inside the lumen can increase the pressure differential between the lumen and the exterior atmosphere. The woven structure can be formed in such a way that an increase in pressure differential between the lumen and the atmosphere causes the woven structure to axially shorten. The woven structure is formed in such a way that axial shortening of the woven structure shortens the length of the tip and increases the distal radius. The increase of the distal radius of the tip is expected to facilitate the aspiration of tissue fragments that can cause an occlusion into the aspiration channel for removal from the eye. In traditional phacoemulsification aspiration channels, an occlusion can cause an increase in negative pressure inside the lumen followed by a sudden outflow of fluid and tissue fragments from the anterior chamber of the eye into the aspiration channel when the occlusion is aspirated. The lengthening of the distal radius of the flexible and expandable tip is expected to reduce sudden outflow from the anterior chamber into the aspiration channel when the distal end becomes occluded. An occlusion causes the distal radius to increase, and the increase of the distal radius facilitates the aspiration of the occlusion. The flexible and expandable nature of the distal end allows the distal end to conform around an occlusion while an occlusion is aspirated, which further facilitates aspiration of an occlusion. Facilitation of the aspiration of an occlusion is expected to reduce sudden outflow from the anterior chamber in the aspiration channel.

According to other example embodiments, the cylindrical woven structure may have a structure similar to that of two interlaced opposite handed helices or an expandable cable sleeve.

According to another example embodiment of the invention, the flexible/expandable tip is made at least partially of a resilient polymer or elastomeric. According to this example embodiment, when the lumen diameter of the flexible/expandable tip increases the walls of the flexible/expandable tip become thinner thus accommodating the expansion. Acrylic/ethylene copolymers (AEM) fluoroelastomers (FKM) and perfluoroelastomers (FFKM) such as those manufactured by DuPont Corporation can be utilized. For example, neoprene, Viton®, Varnac® ethylene acrylic elastomer, ethylene methyl acrylate copolymer with cure site monomer, Kalrez® (FFKM) elastomer may prove useful. According to another example embodiment, the flexible/expandable tip can be formed from a highly stretchable and highly resilient polymer-clay nanocomposite hydrogel. Such materials can be synthesized by in situ polymerization of acrylamide in the presence of pristine montmorillonite (MMT) or chitosan-treated MMT nanoplatelets at elevated temperature. Other elastomers may be used as well. Such a resilient polymer may also be combined with a mesh material or woven structure as described elsewhere in this application.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 5 is a perspective view of a flexible and expandable aspiration tip including a woven structure according to an example embodiment of the present invention;

Figure 1:
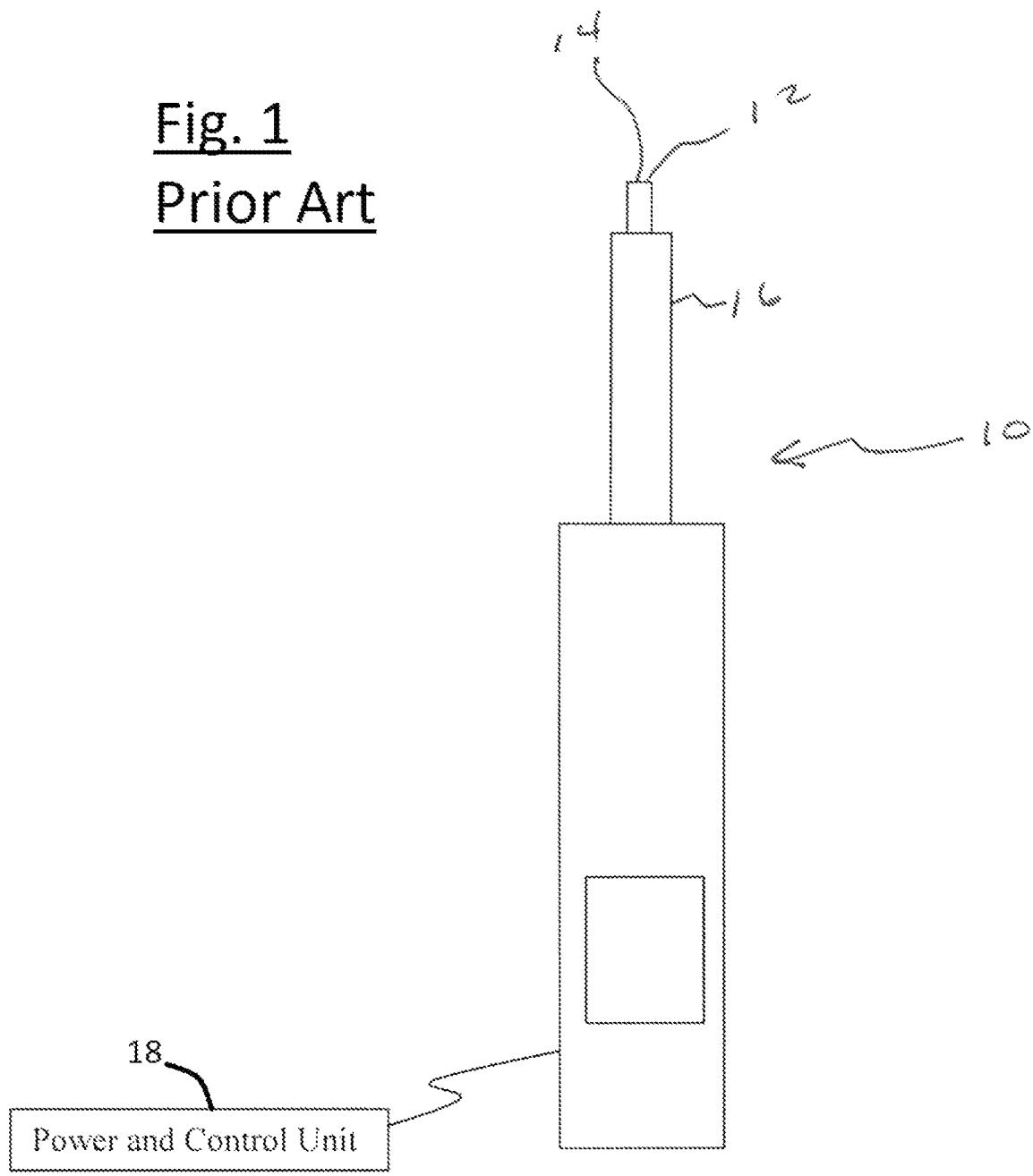
FIG. 1 is a schematic depiction of a typical prior art phacoemulsification handpiece.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Referring to FIG. 1, phacoemulsification handpiece 10 according to the prior art generally includes cutting tip 12, aspiration tube 14, and irrigation passage 16. In the depicted embodiment, irrigation passage 16 generally annularly surrounds aspiration tube 14 and cutting tip 12 extends outwardly beyond irrigation passage 16. Power and control unit 18 supplies energy which serves to ultrasonically vibrate cutting tip 12. Generally, cutting tip 12 of aspiration tube 14 according to the prior art may have a somewhat sharper edge or some structure to facilitate cutting and removal of material.

Figure 2:
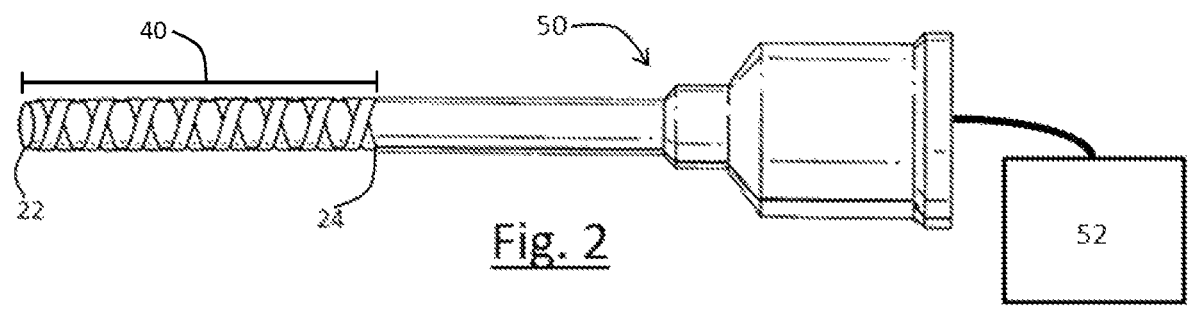
FIG. 2 is a perspective view of a flexible and expandable aspiration tip according to an example embodiment of the invention.
Figure 3:
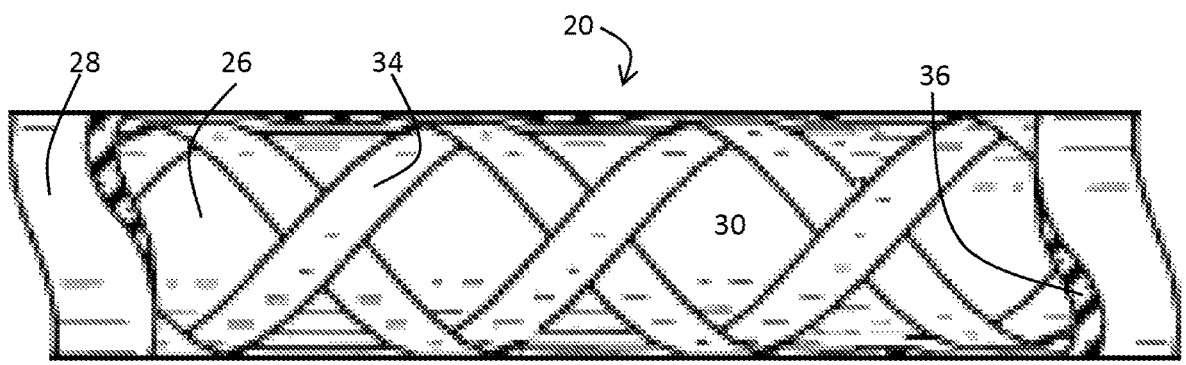
FIG. 3 is a perspective partially cut-away view of a flexible and expandable aspiration tip according to an example embodiment of the invention.

Referring to FIGS. 2 and 3, flexible and expandable tip 20 according to an example embodiment of the invention is depicted. Flexible and expandable tip 20 is a substantially cylindrical structure formed as a hollow tube having wall 29 defining lumen 30 therein. Flexible and expandable tip 20 presents interior surface 26 and exterior surface 28. Interior surface 26 surrounds and defines lumen 30. Exterior surface 28 covers the entire exterior circumference of flexible and expandable tip 20. Flexible and expandable tip 20 includes distal end 22 and proximal end 24. Distal end 22 is cylindrically shaped and is flexible and expandable. Distal end 22 serves as an ultrasonic cutting tip. Flexible and expandable tip 20 is coupled to phacoemulsification device 50 at proximal end 24. Phacoemulsification device 50 is operably coupled to power, suction, and control unit 52. Power, suction, and control unit 52 supplies energy which serves to ultrasonically vibrate distal end 22. Power, suction, and control unit 52 supplies suction for aspiration via flexible and expandable tip 20.

Figure 4:
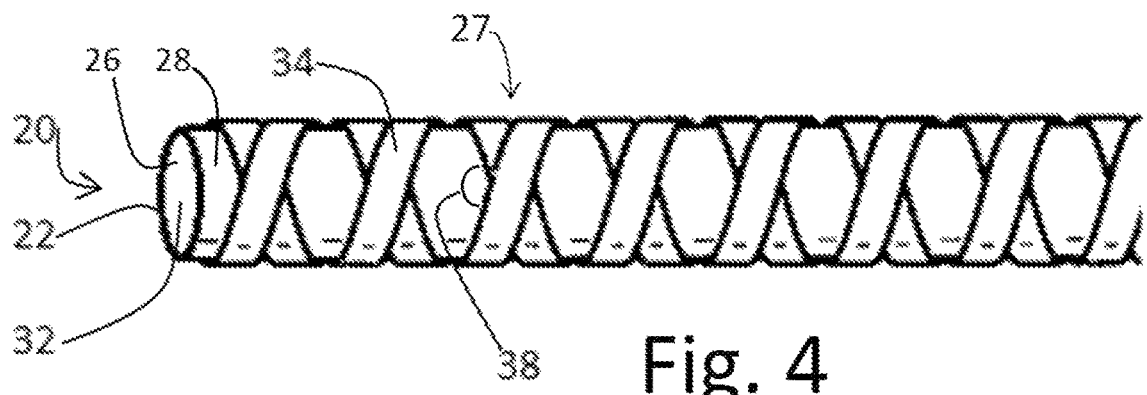
FIG. 4 is a perspective view of a flexible and expandable aspiration tip including a woven structure according to an example embodiment of the invention.

Referring to FIGS. 3 and 4, flexible and expandable tip 20 according to an example embodiment of the invention is depicted. Generally, flexible and expandable tip 20 includes woven structure 27. Woven structure 27 is a substantially cylindrical hollow structure having lumen 30 therein. Woven structure 27 includes interlaced material 34. Interlaced material 34 can have a spiral or helical form. Interlaced material 34 can be formed of metal filaments, polymer fibers, or other suitable material of sufficient strength and flexibility. Spiral or helical shaped interlaced material 34 is woven to form woven structure 27. Interlaced material 34 can be coated with or embedded in an elastomeric polymer 36. Distal end 22 defines mouth of the opening 32. Mouth of the opening 32 is in fluid communication with lumen 30.

Referring to FIGS. 2, 4, and 5, flexible and expandable tip 20 according to an example embodiment of the invention is depicted. Generally flexible and expandable tip 20 includes woven structure 27. Woven structure 27 presents length 40, radius of distal end 42, and angle 38 between interlaced material 34. Woven structure 27 is flexible and formed in such a way that woven structure 27 can shorten along the axis of the cylinder 39 so that distal end 22 is drawn towards proximal end 24. As woven structure 27 shortens along axis of the cylinder 39, length 40 shortens. As woven structure 27 shortens along axis of the cylinder 39, distal end 22 expands radially outward so that radius of distal end 42 increases. As woven structure 27 shortens along axis of the cylinder 39, an angle 38 between interlaced material 34 increases. In general, woven structure 27 is formed in such a way that distal radius 42 increases as length 40 shortens. Woven structure 27 has a resilient nature so that flexible and expandable tip 20 tends to return to its original cylindrical shape following an axial shortening.

Figure 6A:
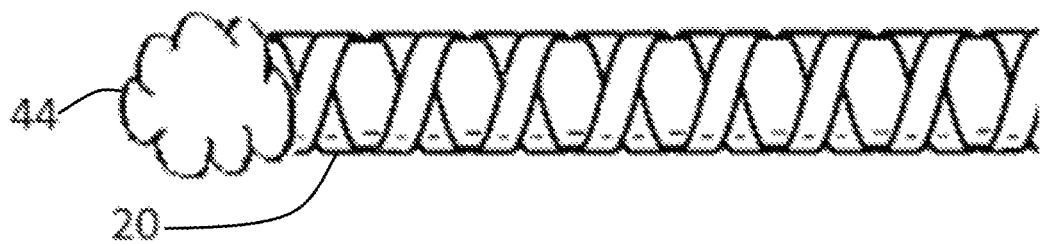
FIG. 6A is a perspective view of a flexible and expandable aspiration tip of an example embodiment of the present invention with a tissue fragment occlusion at the distal end.
Figure 6B:
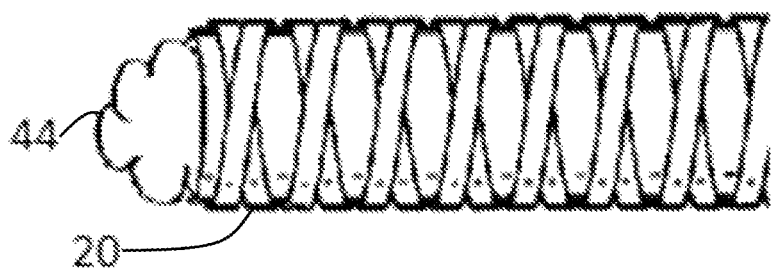
FIG. 6B is a perspective view of a flexible and expandable aspiration tip of an example embodiment of the present invention showing the lengthening of the radius of the distal end caused by an occlusion.
Figure 6C:
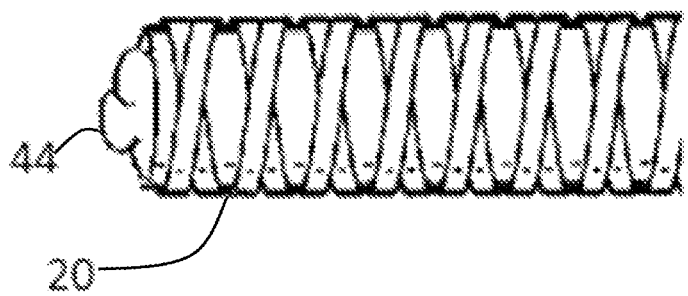
FIG. 6C is a perspective view of a flexible and expandable aspiration tip of an example embodiment of the present invention showing the distal end conforming around an occlusion being aspirated.

Referring to FIGS. 6A, 6B, and 6C, flexible and expandable tip 20, according to an example embodiment of the invention, is depicted. Generally, larger tissue fragment 44 can cause an occlusion at mouth of the opening 32. An occlusion by tissue fragment 44 can cause an increase in negative pressure inside lumen 30 generated by power, suction, and control unit 52. An increase in negative pressure inside lumen 30 increases a pressure differential between lumen 30 and an exterior atmosphere. Woven structure 27 is formed in such a way that a pressure differential increase between lumen 30 and an exterior atmosphere causes woven structure 27 to axially shorten. Axial shortening of woven structure 27 causes radius 42 of distal end 22 to increase. Generally, an occlusion by tissue fragment 44 causes radius 42 of distal end 22 to increase. Lengthening of radius 42 facilitates aspiration of tissue fragment 44. The flexible and expandable nature of distal end 22 allows distal end 22 to conform around an tissue fragment 44 while an tissue fragment 44 is aspirated. Distal end 22 conforming around tissue fragment 44 while tissue fragment 44 is aspirated further facilitates aspiration of tissue fragment 44.

The invention further includes an example method of mitigating surges of flow into and through an aspiration channel during a phacoemulsification process. The method includes utilizing a phacoemulsification cutting tip having a flexible and expandable tip portion; making contact between the flexible and expandable tip portion and a crystalline lens of the eye or fragments of the crystalline lens of the eye; and utilizing an aspiration flow and negative pressure that facilitates radial expansion of the flexible and expandable tip portion upon blockage of an opening of the flexible and expandable tip portion by the fragments of the crystalline lens of the eye.

The invention further includes an example method of phacoemulsification, including contacting a crystalline lens of an eye with a phacoemulsification tip having a distal expandable portion and a proximal rigid portion; and increasing a radius of the expandable portion while shortening and axial length of the expandable portion under negative pressure upon a blockage of an opening of the distal expandable portion; whereby aspiration of crystalline lens fragments is facilitated.

In operation, phacoemulsification device 50 equipped with flexible and expandable tip 20 is applied through an incision in the eye and through a capsulorhexis opening made in the lens capsule of an eye to the crystalline lens therein. Typically, the crystalline lens will be affected by a cataract though clear lens extraction is sometimes performed. When distal end 22 is contacted against a crystalline lens of the eye, ultrasonic vibration of distal end 22 can cause tissue to fragment. Power, suction, and control unit 52 supplies vacuum to flexible and expandable tip 20 to facilitate the aspiration of fluid and tissue fragments separated from the crystalline lens by distal end 22 via lumen 30 and mouth of the opening 32.

According to another example embodiment of the invention, flexible/expandable tip 20 is made at least partially of a resilient polymer or elastomeric. According to this example embodiment, when the radius of distal end 42 of flexible/expandable tip 20 increases the wall 29 of the flexible/expandable tip become thinner thus accommodating the expansion. Acrylic/ethylene copolymers (AEM) fluoroelastomers (FKM) and perfluoroelastomers (FFKM) such as those manufactured by DuPont Corporation can be utilized. For example, neoprene, Viton®, Varnac® ethylene acrylic elastomer, ethylene methyl acrylate copolymer with cure site monomer or Kalrez® (FFKM) elastomer may prove useful. According to another example embodiment, flexible/expandable tip 20 can be formed from a highly stretchable and highly resilient polymer-clay nanocomposite hydrogel. Such materials can be synthesized by in situ polymerization of acrylamide in the presence of pristine montmorillonite (MMT) or chitosan-treated MMT nanoplatelets at elevated temperature. Other elastomers may be used as well. Such a resilient polymer may also be combined with mesh material, interlaced material or woven structure 27 as described elsewhere in this application.

In operation, tissue fragments can be drawn into lumen 30 for aspiration. It is expected that during operation, increasing of radius 42 of distal end 22 will increase the likelihood that fragments of the crystalline lens will be drawn into lumen 30 for more efficient aspiration than in a conventional phacoemulsification aspiration tube 14. Furthermore, more efficient aspiration of tissue fragments will reduce interference with the surgeon's ability to see the lens and other structures of the eye.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art.

Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A phacoemulsification cutting tip, comprising:
    a rigid tubular portion and a flexible and expandable tip portion located distal to the rigid tubular portion;
    the flexible and expandable tip portion defining a distal opening at a distal end thereof, the distal opening being flexibly expandable along with the expandable tip portion; and
    wherein the flexible and expandable tip portion further comprises a woven structure whereby aspiration of crystalline lens fragments is facilitated by expansion of the distal opening to accommodate aspiration of the crystalline lens fragments that are larger than distal opening when the distal opening is unexpanded that may at least partially block the distal opening when unexpanded.

2. The phacoemulsification cutting tip as claimed in claim 1, wherein the woven structure further comprises a cylindrical, helically wound, biaxial braid.

3. The phacoemulsification cutting tip as claimed in claim 1, wherein the woven structure further comprises a spiral or helix shaped material.

4. The phacoemulsification cutting tip as claimed in claim 1, wherein the flexible and expandable tip portion further comprises metal filaments, polymer fibers, polyaramid or para-aramid.

5. The phacoemulsification cutting tip as claimed in claim 1, wherein the flexible and expandable tip portion further comprises an elastomeric material or a resilient material, wherein the elastomeric material or the resilient material biases the flexible and expandable tip portion toward an extended axial length and an unexpanded radius such that the flexible and expandable to portion tends to return to its original cylindrical shape following an axial shortening.

6. The phacoemulsification cutting tip as claimed in claim 1, wherein the flexible and expandable tip portion further comprises a helix shaped material interlaced to form the woven structure.

7. The phacoemulsification cutting tip as claimed in claim 1, wherein the flexible and expandable tip portion facilitates aspiration of crystalline lens fragments by radial expansion and axial shortening of the flexible and expandable tip portion.

8. A method of mitigating surges of flow into and through an aspiration channel during a phacoemulsification process, the method comprising:

utilizing a phacoemulsification cutting tip having a flexible and expandable tip portion with an expandable opening at a distal end of the flexible and expandable tip portion;

making contact between the flexible and expandable tip portion and a crystalline lens of the eye or fragments of the crystalline lens of the eye and facilitating aspiration of the fragments of the crystalline lens that might at least partially block the expandable opening by expanding the opening and the flexible expandable tip portion upon contact of the opening with the crystalline lens or the fragments of the crystalline lens; and making or selecting the phacoemulsification cutting tip flexible and expandable tip portion to include a woven structure.

9. The method as claimed in claim 8 further comprising, making or selecting the woven structure to include a cylindrical, helically wound, biaxial braid.

10. The method as claimed in claim 8 further comprising, making or selecting the woven structure to include a spiral or helix shaped material.

11. The method as claimed in claim 8 further comprising, making or selecting the phacoemulsification cutting tip flexible and expandable tip portion to include an elastomeric material or a resilient material that biases the flexible and expandable tip portion toward an extended axial length and an unexpanded radius such that the flexible and expandable to portion tends to return to its original cylindrical shape following an axial shortening.

12. The method as claimed in claim 8 further comprising, making or selecting the phacoemulsification cutting tip flexible and expandable tip portion to include helix shaped material interlaced to form the woven structure.

13. The method as claimed in claim 8 further comprising facilitating aspiration of crystalline lens fragments by radial expansion and axial shortening of the flexible and expandable tip portion.

14. A method of phacoemulsification, comprising:

contacting a crystalline lens of an eye with a distal expandable portion of a phacoemulsification tip having the distal expandable portion and an expandable opening at a distal end of the distal expandable portion and a proximal rigid portion; and making or selecting the phacoemulsification cutting tip flexible and expandable tip portion to include a woven structure thereby facilitating radial expansion and axial length shortening of the flexible and expandable tip portion in response to fragments of the crystalline lens that might at least partially block the expandable opening by expanding the opening and the flexible expandable tip portion upon contact of the opening with the crystalline lens or the fragments of the crystalline lens;

whereby aspiration of crystalline lens fragments is facilitated.

15. The method as claimed in claim 14 further comprising, making or selecting the woven structure to include a cylindrical, helically wound, biaxial braid.

16. The method as claimed in claim 14 further comprising, making or selecting the woven structure to include a spiral or helix shaped material.

17. The method as claimed in claim 14 further comprising, making or selecting the woven structure to include an elastomeric material or a resilient material that biases the flexible and expandable tip portion toward an extended axial length and an unexpanded radius such that the flexible and expandable to portion tends to return to its original cylindrical shape following an axial shortening.

18. The method as claimed in claim 14 further comprising, making or selecting the phacoemulsification cutting tip flexible and expandable tip portion to include helix shaped material interlaced to form the woven structure.

\* \* \* \* \*